US010131364B2

(12) United States Patent
Seder et al.

(10) Patent No.: US 10,131,364 B2
(45) Date of Patent: Nov. 20, 2018

(54) AMBIENT DISPLAY

(71) Applicant: GM GLOBAL TECHNOLOGY OPERATIONS LLC, Detroit, MI (US)

(72) Inventors: Thomas A. Seder, Northville, MI (US); Joseph F. Szczerba, Grand Blanc, MI (US); Roy J. Mathieu, Rochester Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 411 days.

(21) Appl. No.: 14/920,499

(22) Filed: Oct. 22, 2015

(65) Prior Publication Data

US 2016/0085070 A1   Mar. 24, 2016

Related U.S. Application Data

(63) Continuation of application No. PCT/US2014/035387, filed on Apr. 25, 2014.
(Continued)

(51) Int. Cl.
*G02B 27/14* (2006.01)
*G03H 1/00* (2006.01)
(Continued)

(52) U.S. Cl.
CPC ............ *B60W 50/14* (2013.01); *A61B 3/113* (2013.01); *A61B 5/0205* (2013.01); *A61B 5/6893* (2013.01); *B60C 9/00* (2013.01); *B60K 28/066* (2013.01); *B60K 35/00* (2013.01); *G02B 6/005* (2013.01); *G02B 27/0101* (2013.01);
(Continued)

(58) Field of Classification Search
CPC ............ G02B 27/0172; G02B 27/0101; G02B 2027/0178; G02B 2027/0132; G02B 2027/011; G02B 27/01
USPC ................ 359/603–636, 409–410, 462, 466, 359/638–639, 13–14, 404, 407; 348/115; 345/7, 9, 156; 349/11; 701/1; 310/49 R,
(Continued)

(56) References Cited

U.S. PATENT DOCUMENTS 5,883,605 A * 3/1999 Knapp ................. B60R 1/088
  345/102
2002/0074932 A1* 6/2002 Bouchard ............. B82Y 10/00
  313/495
(Continued)

FOREIGN PATENT DOCUMENTS

JP   H08272321 A   10/1996

*Primary Examiner* — Dawayne A Pinkney
(74) *Attorney, Agent, or Firm* — Harness, Dickey & Pierce, P.L.C.

(57) ABSTRACT

A windshield includes a windshield body and an ambient display coupled to the windshield body. The ambient display includes a light guide plate and a light source optically coupled to the light source. Aside from the light source, the ambient display includes a transparent phosphor film and an optic array. The transparent phosphor film includes at least one phosphor. The optic array includes a plurality of lenses and is disposed between the light guide plate and the transparent phosphor film. The light guide plate is positioned relative to the optic array such that light emitted from the light source is directed toward the optic array. The chromaticity and luminance of the light emitted by the transparent phosphor film can be adjusted based on the electrical current received by the light source.

21 Claims, 2 Drawing Sheets

Related U.S. Application Data

(60) Provisional application No. 61/816,089, filed on Apr. 25, 2013.

(51) Int. Cl.
| | |
|---|---|
| G02B 27/00 | (2006.01) |
| H04N 7/00 | (2011.01) |
| G09G 5/00 | (2006.01) |
| G02F 1/1335 | (2006.01) |
| G01C 21/00 | (2006.01) |
| B60W 50/14 | (2012.01) |
| B60K 35/00 | (2006.01) |
| B60K 28/06 | (2006.01) |
| B60C 9/00 | (2006.01) |
| G06K 9/00 | (2006.01) |
| G05D 3/00 | (2006.01) |
| G08C 17/02 | (2006.01) |
| A61B 3/113 | (2006.01) |
| A61B 5/0205 | (2006.01) |
| A61B 5/00 | (2006.01) |
| G07C 5/02 | (2006.01) |
| G07C 5/08 | (2006.01) |
| F21V 8/00 | (2006.01) |
| G02B 27/01 | (2006.01) |
| G02B 27/09 | (2006.01) |
| A61B 5/024 | (2006.01) |
| A61B 5/053 | (2006.01) |

(52) U.S. Cl.
CPC ..... *G02B 27/0927* (2013.01); *G02B 27/0961* (2013.01); *G05D 3/00* (2013.01); *G06K 9/00845* (2013.01); *G07C 5/02* (2013.01); *G07C 5/08* (2013.01); *G08C 17/02* (2013.01); *A61B 5/02405* (2013.01); *A61B 5/0533* (2013.01); *B60K 2350/2013* (2013.01); *B60K 2350/2021* (2013.01); *B60K 2350/2052* (2013.01); *B60K 2350/352* (2013.01); *B60R 2300/8006* (2013.01); *B60R 2300/8093* (2013.01); *B60W 2050/146* (2013.01); *B60Y 2302/03* (2013.01); *G02B 2027/0112* (2013.01); *G02B 2027/0118* (2013.01); *G02B 2027/0141* (2013.01); *G02B 2027/0194* (2013.01)

(58) Field of Classification Search
USPC ......... 310/156.32, 156.35, 266–268, 156.02; 340/438, 980, 995.1, 815.47, 815.74
See application file for complete search history.

(56) References Cited

U.S. PATENT DOCUMENTS

| | | | |
|---|---|---|---|
| 2006/0146518 A1* | 7/2006 | Dubin | G02B 6/0008 362/106 |
| 2008/0158510 A1 | 7/2008 | Tant et al. | |
| 2009/0116107 A1* | 5/2009 | Kindler | G02B 26/123 359/457 |
| 2011/0025584 A1 | 2/2011 | Nishigasako et al. | |
| 2012/0068083 A1 | 3/2012 | Labrot et al. | |
| 2014/0355106 A1* | 12/2014 | Laluet | B60J 1/02 359/359 |

\* cited by examiner

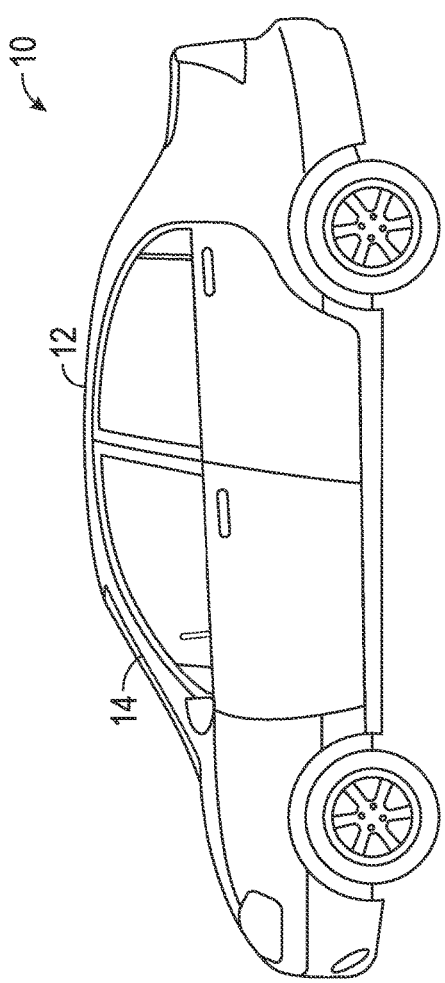
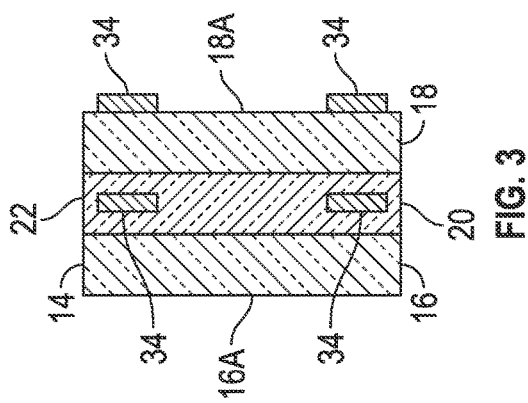
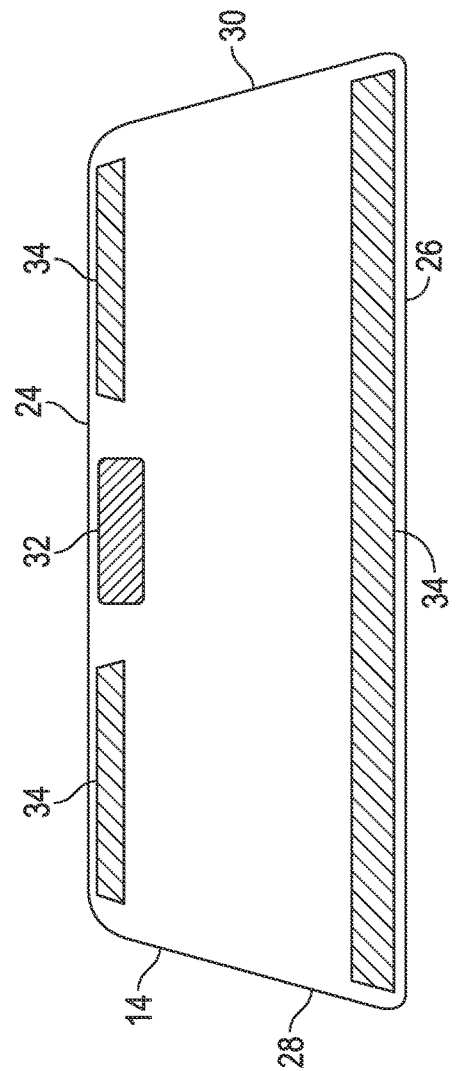

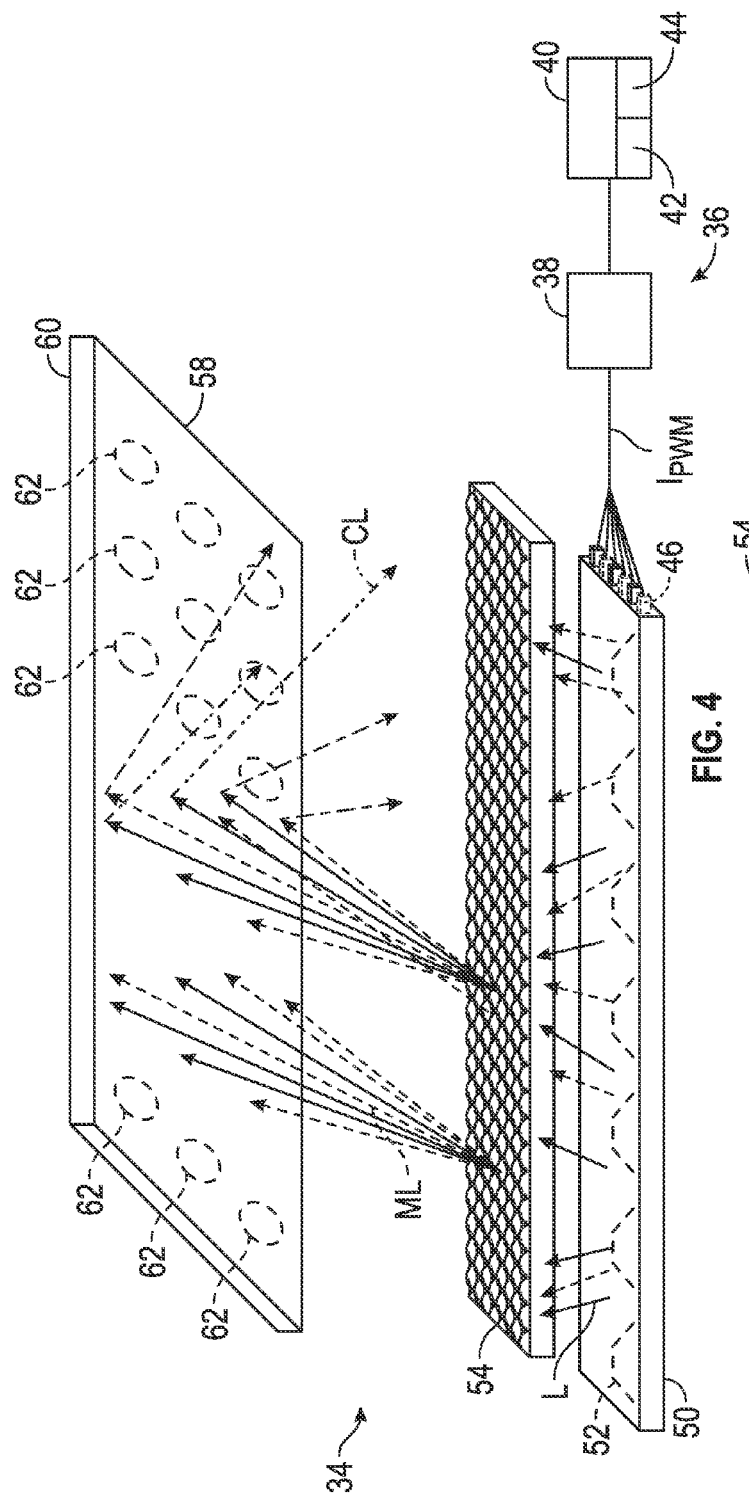
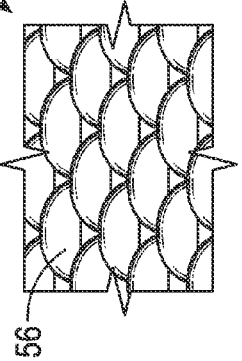
FIG. 4
FIG. 5

AMBIENT DISPLAY

CROSS-REFERENCE TO RELATED APPLICATIONS

This application is a bypass continuation of, and claims priority to, International Patent Application No. PCT/US2014/035387, filed on Apr. 25, 2014, which in turn claims priority to and the benefit of U.S. Provisional Application No. 61/816,089, filed Apr. 25, 2013, each of which is hereby incorporated by reference in its entirety.

TECHNICAL FIELD

The present disclosure relates to ambient displays for use in a vehicle.

BACKGROUND

Vehicles, such as cars, typically include displays or indicators to provide information to the vehicle operator. Such displays or indicators may, for example, provide information regarding mileage, fuel consumption, and vehicle speed. The vehicle operator can observe an in-vehicle display in order to visually process the information presented by these displays or indicators.

SUMMARY

It is therefore useful to develop an ambient display that allows the vehicle operator to visually process the information presented by the ambient displays. Specifically, it is useful to develop substantially transparent ambient displays that are coupled to the windshield of the vehicle and are optimally located relative to the windshield in the forward field of view (FOV) of the vehicle operator to encourage the vehicle operator to look forward through the windshield. It is also useful to minimize the cost of these ambient displays. To this end, the present disclosure describes an ambient display capable of being coupled to a vehicle windshield, as well as a windshield including at least one ambient display.

In an embodiment, the windshield includes a first glass layer, a second glass layer, and an interlayer disposed between the first and second glass layers. At least the first glass layer, the second glass layer, and the interlayer collectively form a windshield body. The windshield further includes at least one ambient display coupled to the windshield body. The ambient display includes a light guide plate and a light source optically coupled to the light guide plate such that the light emitted from the light source is received by the light guide plate. Aside from the light source, the ambient display includes a transparent phosphor film and a micro-optic array. The transparent phosphor film includes at least one phosphor. The micro-optic array includes a plurality of lenses and is disposed between the light source and the transparent phosphor film such that the optic array shapes a distribution of light guided by the light guide plate according to the shape and size of the transparent phosphor film. The light guide plate is positioned relative to the optic array such that light emitted from the light source is directed toward the optic array. The chromaticity and luminance of the light emitted by the transparent phosphor film can be adjusted based on the electrical current received by the light source.

The present disclosure also relates to a vehicle including a vehicle body, a windshield coupled to the vehicle body, a power supply, a control module in communication with the power supply, and an ambient display as described above. The control module is specifically programmed to adjust the electrical current supplied to light source in order to adjust the chromaticity and luminance of the light emitted by the transparent phosphor film.

The present disclosure also relates to an ambient display system including the power supply, control module, and ambient display as described above. The ambient display can be coupled to a windshield as described above.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 1 is a schematic, side view of a vehicle including a windshield;

FIG. 2 is a schematic, front view of the windshield of the vehicle schematically shown in FIG. 1, wherein the windshield includes a plurality of ambient displays;

FIG. 3 is a schematic, sectional side view of the windshield of FIG. 1;

FIG. 4 is a schematic, perspective, exploded view of one of the ambient displays schematically illustrated in FIG. 2, wherein the ambient display is electrically connected to a power supply, and the power supply is in communication with a control module; and FIG. 5 is a schematic, perspective, enlarged view of a micro-optic array of the ambient display shown in FIG. 4.

DETAILED DESCRIPTION

Referring now to the drawings, wherein the like numerals indicate corresponding parts throughout the several views, FIG. 1 schematically illustrates a vehicle 10 including a vehicle body 12. The vehicle 10 may be a land vehicle, such as a car, farm equipment, construction equipment, or any other type of vehicle such as an airplane or a boat. Regardless of the specific kind of vehicle, the vehicle 10 includes a windshield 14 coupled to the vehicle body 12. The windshield 14 is wholly or partly made of a substantially transparent material. Accordingly, a vehicle operator can see through the windshield 14.

With respect to FIGS. 2 and 3, the windshield 14 includes a first glass layer 16, a second glass layer 18, and an interlayer 20 disposed between the first and second glass layers 16, 18. In the depicted embodiment, the interlayer 20 is wholly or partly made of polyvinyl butyral (PVB) and interconnects the first and second glass layers 16, 18. The first glass layer 16, the second glass layer 18, and the interlayer 20 collectively form a windshield body 22 and are substantially transparent in order to allow a vehicle operator to see through the windshield body 22. The interlayer 20 is disposed between the first and second glass layers 16, 18. In the depicted embodiment, the interlayer 20 interconnects the first and second glass layers 16, 18.

With continued reference to FIGS. 2 and 3, the windshield 14 defines a top edge 24, a bottom edge 26 opposite the top edge 24, a first lateral edge 28 located between the top edge 24 and the bottom edge 26, and second lateral edge 30 opposite the first lateral edge 28. A rearview mirror 32 is coupled to the windshield 14 between the first lateral edge 28 and the second lateral edge 30.

The vehicle 10 further includes at least one ambient display 34 coupled to the windshield 14. In the depicted embodiment, the vehicle 10 includes three ambient displays 34 coupled to the windshield body 22. It is nevertheless contemplated that the vehicle 10 may include more or fewer ambient displays 34. Irrespective of the quantity, the ambient displays 34 are located relative to the windshield 14 along the peripheral visual field of the vehicle operator (i.e. the driver). In particular, the location of the ambient displays 34 relative to the windshield 14 allows the vehicle operator to visually process the indications in the ambient displays 34 without foveation. In the present disclosure, the term "foveation" means the act of angling the eyes to center the visual field of view on an object to focus and maximize visual acuity. Thus, the ambient displays 34 are optimally located relative to the windshield 14 in the edge of the forward field of view (FOV) of the vehicle operator to encourage the vehicle operator to look forward through the windshield 14. To this end, in the depicted embodiment, two ambient displays 34 are adjacent to the top edge 24 of the windshield 14 and another ambient display 34 is adjacent the bottom edge 26 of the windshield 14. One ambient display 34 is positioned closer the first lateral edge 28 than to the second lateral edge 30. Another ambient display 34 is disposed closer to the second lateral edge 30 than to the first lateral edge 28. Yet another ambient display 34 is positioned substantially equidistant from the first and second lateral edges 28, 30.

Each ambient display 34 is substantially transparent such that the visible internal light transmission through the ambient display 34 is greater than ninety (90) percent, thereby allowing the vehicle operator to see through the ambient display 34. In other words, each ambient display 34 is wholly or partly made of one or more substantially transparent materials in order to allow a vehicle operator to see through the ambient display 34. Further, each ambient display 34 can present information through color. For instance, the ambient displays 34 may change colors along the red-green-blue color spectrum or the red-green color spectrum to indicate particular information to the vehicle operator. As a non-limiting example, at least one ambient display 34 may change colors to red in order to indicate that another vehicle is close to the vehicle 10. Aside from changing colors, the ambient displays 34 can change its luminance at a constant rate to indicate other types of information to the vehicle operator. For example, at least one ambient display 34 can increase its luminance as another vehicle gets closer to the vehicle 10. In addition to changing its luminance at a constant rate, each ambient display 34 can modulate its luminance at a predetermined constant or variable frequency to indicate other types of information to the vehicle operator. For example, each ambient display 34 can modulate its luminance at an increasing frequency to indicate to the vehicle operator the rate at which another vehicle is approaching the vehicle 10.

With specific reference to FIG. 3, the ambient displays 34 can be coupled to an outer surface 16A, 18A of the first glass layer 16 or the second glass layer 18. As a non-limiting example, the ambient displays 34 can be laminated to the outer surface 16A, 18A of the first glass layer 16 or the second glass layer 18. Alternatively or additionally, the ambient displays 34 can be coupled to the interlayer 20. As a non-limiting example, the ambient displays 34 can be at least partially embedded inside the interlayer 20. In the depicted embodiment, the ambient displays 34 are completely embedded inside the interlayer 20.

With reference to FIGS. 4 and 5, each ambient display 34 is part of an ambient display system 36, which also includes a power supply 38 and a control module 40. The power supply 38 is electrically connected to the ambient display 34 and can therefore supply an electrical current to the ambient display 34. The control module 40 is in communication (e.g., electronic communication) with the power supply 38 and can regulate the electrical current supplied by the power supply 38. The terms "control module," "control," "controller," "control unit," "processor" and similar terms mean any one or various combinations of one or more of Application Specific Integrated Circuit(s) (ASIC), electronic circuit(s), central processing unit(s) (preferably microprocessor(s)) and associated memory and storage (read only, programmable read only, random access, hard drive, etc.) executing one or more software or firmware programs or routines, combinational logic circuit(s), sequential logic circuit(s), input/output circuit(s) and devices, appropriate signal conditioning and buffer circuitry, and other components to provide the described functionality. "Software," "firmware," "programs," "instructions," "routines," "code," "algorithms" and similar terms mean any controller executable instruction sets including calibrations and look-up tables. In the depicted embodiment, the control module 40 includes at least one processor 42 and at least one memory 44 (or any non-transitory, tangible computer readable storage medium). The memory 44 can store controller executable instruction sets, and the processor 42 can execute the controller executable instruction sets stored in the memory 44. In the depicted embodiment, the control module 40 is programmed to control the electrical current supplied by the power supply 38. The power supply 38 can then supply electrical current to the ambient display 34.

Each ambient display 34 includes at least one light source 46 electrically connected to the power supply 38. As such, the power supply 38 can supply electrical current to the light source 46. Upon receipt of the electrical current from the power supply 38, the light source 46 emits light. In the depicted embodiment, the light sources 46 are light-emitting diodes (LEDs). The light source 46 (e.g., LEDs) may emit violet or near ultraviolet radiation at a specific wavelength to induce fluorescence by the phosphor 62. Depending on the chemical identity and spectral characteristics of the phosphor 62 it may emit (fluoresce) in the red, green or blue regions of the visible spectrum subsequent to absorption of the radiation produced by the LEDs. Accordingly, there is a specific LED whose emission is matched to the absorption spectrum of each specific red, green or blue phosphor 62.

The ambient display 34 further includes a frustrated total internal reflection light guide plate 50 optically coupled to the light sources 46. As such, light emitted by the light sources 46 is received by the light guide plate 50. In the depicted embodiment, the light source 46 (e.g., LEDs) are at least partially embedded in the light guide plate 50, thereby allowing the light emitted by the light source 46 (e.g., LEDs) to be received efficiently by the light guide plate 50. Light guide plate-LED optical coupling can be achieved with non-embedded LEDs, though with less coupling efficiency. The light guide plate 50 includes at least one frustration facet 52 for frustrating the total internal reflection in the light guide plate 50. In other words, the frustration facets 52 allow the light to escape from the light guide plate 50 and direct the light L toward an optic array 54 of the ambient display 34.

Each ambient display 34 also includes the optic array 54, which may be a micro-optic array. The optic array 54 includes a plurality of lenses 56 (FIG. 5) capable of magnifying the light L emitted by the light source 46. The lenses 56 may be spherical lenses (as shown in FIG. 5) or cylindrical lenses. Regardless of the shape of lenses 56, the optic array 54 can shape the distribution of light guided by the light guide plate 50 according to the shape and size of a transparent phosphor film 58 of the ambient display 34. Thus, the optic array 54 can receive light L from the light guide plate 50 and direct magnified light ML to the transparent phosphor film 58. To this end, the optic array 54 is disposed between the light guide plate 50 and the transparent phosphor film 58. Accordingly, the optic array 54 can shape the distribution of the light guided by the light guide plate 50 according to the shape and size of the transparent phosphor film 58. The light guide plate 50 is positioned relative to the optic array 54 such that light emitted from the light sources 46 is directed toward the optic array 54.

The substantially transparent phosphor film 58 includes a substantially transparent substrate 60 in order to allow the vehicle operator to see through the transparent phosphor film 58. As a non-limiting example, the substantially transparent substrate 60 may be partly or wholly made of amorphous polyethylene terephthalate (PET). The visible light internal transmission through the transparent phosphor film 58 is greater than ninety (90) percent in order to allow the vehicle operator to see through the ambient display 34. The transparent phosphor film 58 includes at least one phosphor 62 at least partially embedded in the substantially transparent substrate 60. As used herein, the term "phosphor" refers to a substance that exhibits the phenomenon of luminescence and includes both phosphorescent materials and fluorescent materials. The phosphors 62 may be organic or inorganic and, in the depicted embodiment, exhibit fluorescence. The phosphors 62 of the substantially transparent phosphor film 58 green phosphor, red phosphor, blue phosphor, or any combination thereof. For example, the green phosphor may be a copper and aluminum activated zinc sulfide (ZnS:Cu, Al). The red phosphor may be, for example, an europium activated yttrium oxide-sulfide ($Y_2O_2S$:Eu). The europium activated yttrium oxide-sulfide may be coated with nano-sized particles of iron oxide ($F_2O_3$). The blue phosphor may be, for example, a zinc sulfide silver (ZnS:Ag). In the substantially transparent phosphor film 58, the phosphor 62 may be distributed evenly along the substantially transparent substrate 60 and each phosphor 62 has a diameter that is less than 100 nanometers in order to enhance visible light transmission through the ambient display 34. In FIG. 4, the phosphors 62 are illustrated quite large with respect to the transparent substrate 60 for illustration purposes only. The phosphors 62 may have specific patterns in order to present icons on the ambient displays 34. The substantially transparent phosphor film 58 may alternatively include quantum dot phosphors.

In operation, the power supply 38 provides electrical current to the light sources 46. In response, the light sources 46 emit ultraviolet or violet light, which is captured by the light guide plate 50. The light guide plate 50 then directs the light toward the optic array 54. Next, the optic array 54 magnifies the light L in accordance with the shape and size of the transparent phosphor film 58 and directs the magnified light ML toward the transparent phosphor film 58. The substantially transparent phosphor film 58 then absorbs the magnified light ML and, depending on the excitation wavelengths of the magnified light ML, emits a colored light CL along the red-green-blue color spectrum. Thus, the ambient display 34 can be color-tuned based, at least in part, on the excitation wavelengths of the light L emitted by the light sources 46.

The control module 40 can control the power supply 38 in order to adjust the electrical current supplied to the light sources 46. In doing so, the control module 40 can adjust the chromaticity or luminance of the colored light CL emitted by the transparent phosphor film 58. By adjusting the electrical current supplied to the light sources 46, the control module 40 can change the color of the colored light CL. In addition, the control module 40 can adjust the luminance of the colored light CL at a constant rate or modulate the luminance of the colored light CL at a constant or variable frequency. To adjust the luminance of the colored light CL emitted by the transparent phosphor film 58, the control module 40 can command the power supply 38 to adjust the magnitude of the electrical current supplied to the light sources 46 at a constant rate. In other words, the control module 40 is programmed to adjust the magnitude of the electrical current supplied by the power supply 38 in order to adjust the luminance of the colored light CL emitted by the substantially transparent phosphor film 58.

The power supply 38 can emit a pulse modulated current $I_{PWM}$, and the control module 40 can control the duty cycle of the pulse modulated current $I_{PWM}$. By adjusting the duty cycle of the pulse modulated current $I_{PW}$, the excitation wavelengths of the light L emitted by the light source 46 (and eventually the magnified light ML) can be adjusted in accordance with instructions stored in the control module 40. As a consequence, the chromaticity of the colored light CL emitted by the substantially transparent phosphor film 58 can be adjusted by adjusting the duty cycle of the pulse modulated current $I_{PWM}$. In summary, the control module 40 can command the power supply 38 to adjust the electrical current supplied to the light sources 46 (e.g., LEDs) in order to adjust luminance, temporal nature of the luminance, the chromaticity, and spatial characteristics of the luminance (patterns) of the ambient display 34. The luminance and chromaticity of the colored light CL emitted by the substantially transparent phosphor film 58 can be adjusted based on the electrical current received by the light sources 46.

While the best modes for carrying out the invention have been described in detail, those familiar with the art to which this invention relates will recognize various alternative designs and embodiments for practicing the invention within the scope of the appended claims. For example, the ambient display 34 can be substituted with a transparent organic LED. The light guide plate 50 and the LEDs can be substituted with the red-green-blue pico (or pocket) projector with a micro-optic projection screen. The light guide plate 50 and the LEDs can be substituted with the violet and near ultraviolet (UV) pico (or pocket) projector with a transparent phosphor screen. The ambient display 34 can be replaced with a transparent electroluminescent (EL) display. Also, a lens-of-lens design can be incorporated in the ambient display 34 in order to present fixed format images. Also, the ambient display 34 can be partly or entirely coupled to the portions of the vehicle body 12, such as the pillars.

The invention claimed is:

1. A windshield for a vehicle, comprising:
   a first glass layer;
   a second glass layer;
   an interlayer disposed between the first and second glass layers, wherein at least the first glass layer, the second glass layer, and the interlayer collectively form a windshield body;
   an ambient display coupled to the windshield body, wherein the ambient display includes:
      a light guide plate;
      a light source optically coupled to the light guide plate such that light emitted from the light source is received by the light guide plate;

a substantially transparent phosphor film including at least one phosphor;

an optic array including a plurality of lenses, the optic array being disposed between the light guide plate and the substantially transparent phosphor film such that the optic array shapes a distribution of light guided by the light guide plate according to a shape and size of the substantially transparent phosphor film, wherein the light guide plate is positioned relative to the optic array such that light emitted from the light source is directed toward the optic array;

wherein a chromaticity and a luminance of light emitted by the substantially transparent phosphor film is adjustable based on an electrical current received by the light source;

a control module programmed to adjust an electrical current supplied to the light source to adjust a temporal nature of the luminance and spatial characteristics of the luminance of the ambient display; and wherein the second glass layer defines an outer surface, the ambient display is directly coupled to the outer surface of the second glass layer, the outer surface of the second glass layer faces away from the interlayer, the outer surface of the second glass layer faces away from the first glass layer, the light source is directly coupled to the light guide plate, the light guide plate includes at least one frustration facet configured to frustrate a total internal reflection in the light guide plate, the optic array is configured to direct magnified light to the substantially transparent phosphor film, and the substantially transparent phosphor film is configured to absorb the magnified light and emit a colored light.

2. The windshield of claim 1, wherein the substantially transparent phosphor film includes a green phosphor.

3. The windshield of claim 2, wherein the substantially transparent phosphor film includes a red phosphor.

4. The windshield of claim 3, wherein the substantially transparent phosphor film includes a blue phosphor.

5. The windshield of claim 4, wherein the luminance of light emitted by the substantially transparent phosphor film is adjustable based on a magnitude of the electrical current received by the light source.

6. The windshield of claim 4, wherein the chromaticity of the light emitted by the substantially transparent phosphor film is adjustable based on a duty cycle of a pulse modulated current received by the light source.

7. The windshield of claim 1, wherein the ambient display is laminated to the outer surface of the second glass layer.

8. The windshield of claim 1, wherein the ambient display is embedded inside the interlayer.

9. The windshield of claim 1, wherein the light source is a plurality of light emitting diodes (LEDs) that are coupled to the light guide plate.

10. A vehicle, comprising:
a vehicle body;
a windshield coupled to the vehicle body;
a power supply;
a control module in communication with the power supply, wherein the control module is programmed to control an electrical current supplied by the power supply;
an ambient display coupled to the windshield, wherein the ambient display includes:
a light guide plate;
a light source electrically connected to the power supply such that the power supply is capable of supplying electrical current to the light source, wherein the light source is optically coupled to the light guide plate such that light emitted from the light source is received by the light guide plate;
a substantially transparent phosphor film including at least one phosphor;
an optic array including a plurality of lenses, the optic array being disposed between the light guide plate and the substantially transparent phosphor film such that the optic array shapes a distribution of light guided by the light guide plate according to a shape and size of the substantially transparent phosphor film, wherein the light guide plate is positioned relative to the optic array such that light emitted from the light source is directed toward the optic array;
wherein the control module is programmed to adjust the electrical current supplied by the power supply in order to adjust a chromaticity and a luminance of light emitted by the substantially transparent phosphor film; and
wherein the windshield includes a first glass layer, a second glass layer, and an interlayer disposed between the first and second glass layers, at least the first glass layer, the second glass layer, and the interlayer collectively form a windshield body, the second glass layer defines an outer surface, the ambient display is directly coupled to the outer surface of the second glass layer, the outer surface of the second glass layer faces away from the interlayer, the outer surface of the second glass layer faces away from the first glass layer, the light source is directly coupled to the light guide plate, the light guide plate includes at least one frustration facet configured to frustrate a total internal reflection in the light guide plate, the optic array is configured to direct magnified light to the substantially transparent phosphor film, the substantially transparent phosphor film is configured to absorb the magnified light and emit a colored light, the control module is programmed to command the power supply to adjust the electrical current supplied to the light source to adjust a temporal nature of the luminance and spatial characteristics of the luminance of the ambient display.

11. The vehicle of claim 10, wherein the control module is programmed to adjust a magnitude of the electrical current supplied by the power supply in order to adjust the luminance of the light emitted by the substantially transparent phosphor film.

12. The vehicle of claim 11, wherein the control module is programmed to adjust a duty cycle of a pulse modulated current received by the light source in order to adjust the chromaticity of the light emitted by the substantially transparent phosphor film.

13. The vehicle of claim 10, wherein the windshield defines a top edge, a bottom edge opposite the top edge, a first lateral edge located between the top edge and the bottom edge, and a second lateral edge opposite the first lateral edge, the second lateral edge is located between the top edge and the bottom edge, the ambient display is a first ambient display, the first ambient display is closer to the top edge than to the bottom edge of the windshield, the vehicle further includes a second ambient display, the second ambient display is closer to the top edge than to the bottom edge of the windshield, the first ambient display is closer to the first lateral edge than to the second lateral edge of the windshield, the second ambient display is closer to the second lateral edge than to the first lateral edge of the windshield, the vehicle includes a third ambient display, the third ambient display is closer to the bottom edge than to the top edge of the windshield, and the third ambient display is equidistant from the first lateral edge and the second lateral edge of the windshield.

14. The vehicle of claim 13, wherein the interlayer is directly coupled to the first glass layer, the interlayer is directly coupled to the second glass layer, the optic array is a micro-optic array, the interlayer is wholly made of polyvinyl butyral, the substantially transparent phosphor film includes a substantially transparent substrate, the substantially transparent substrate is wholly made of amorphous polyethylene terephthalate, a visible light internal transmission through the substantially transparent phosphor film is greater than ninety percent, the at least one phosphor is a plurality of phosphors, the plurality of phosphors is distributed evenly along the substantially transparent substrate, and each of the plurality of phosphors has a diameter that is less than one hundred nanometers in order to enhance visible light transmission through the ambient display.

15. The vehicle of claim 10, wherein the ambient display is embedded inside the interlayer.

16. The vehicle of claim 10, wherein the light source is a plurality of light emitting diodes (LEDs) that are coupled to the light guide plate.

17. The vehicle of claim 10, wherein a visible light transmission of the substantially transparent phosphor film is greater than ninety percent.

18. The vehicle of claim 10, wherein the substantially transparent phosphor film includes a transparent substrate, and the at least one phosphor is at least partially embedded inside the transparent substrate.

19. A windshield, comprising:
a first glass layer;
a second glass layer;
an interlayer disposed between the first and second glass layers, wherein at least the first glass layer, the second glass layer, and the interlayer collectively form a windshield body;
an ambient display coupled to the windshield body, wherein the ambient display includes:
a light guide plate;
a light source optically coupled to the light guide plate such that light emitted from the light source is received by the light guide plate;
a substantially transparent phosphor film including at least one phosphor;
an optic array including a plurality of lenses, the optic array being disposed between the light guide plate and the substantially transparent phosphor film such that the optic array shapes a distribution of light guided by the light guide plate according to a shape and size of the substantially transparent phosphor film, wherein the light guide plate is positioned relative to the optic array such that light emitted from the light source is directed toward the optic array;
wherein a chromaticity and a luminance of light emitted by the substantially transparent phosphor film is adjustable based on an electrical current received by the light source; and
wherein the second glass layer defines an outer surface, the ambient display is directly coupled to the outer surface of the second glass layer, the outer surface of the second glass layer faces away from the interlayer, the outer surface of the second glass layer faces away from the first glass layer, the light source is directly coupled to the light guide plate, the light guide plate includes at least one frustration facet configured to frustrate a total internal reflection in the light guide plate, the optic array is configured to direct magnified light to the substantially transparent phosphor film, and the substantially transparent phosphor film is configured to absorb the magnified light and emit a colored light.

20. The windshield of claim 19, wherein the light source is a plurality of light emitting diodes (LEDs) that are coupled to the light guide plate.

21. The windshield of claim 19, wherein a visible light transmission of the substantially transparent phosphor film is greater than ninety percent.

* * * * *